United States Patent
Perez Lopez et al.

(10) Patent No.: US 10,421,203 B2
(45) Date of Patent: Sep. 24, 2019

(54) ELECTRIC SHAVER

(71) Applicant: Braun GmbH, Kronberg (DE)

(72) Inventors: Cirilo Javier Perez Lopez, Frankfurt am Main (DE); Andreas Erndt, Kelkheim (DE); Gerd Laschinski, Oberursel (DE); Wolfgang Stegmann, Frankfurt am Main (DE)

(73) Assignee: Braun GMBH, Kronberg (DE)

( * ) Notice: Subject to any disclaimer, the term of this patent is extended or adjusted under 35 U.S.C. 154(b) by 61 days.

(21) Appl. No.: 15/714,971

(22) Filed: Sep. 25, 2017

(65) Prior Publication Data

US 2018/0085942 A1    Mar. 29, 2018

(30) Foreign Application Priority Data

Sep. 28, 2016    (EP) .................................. 16191117.7
Sep. 25, 2017    (EP) .................................. 17192805.4

(51) Int. Cl.
*B26B 19/06*      (2006.01)
*B26B 19/38*      (2006.01)
(Continued)

(52) U.S. Cl.
CPC .......... *B26B 19/388* (2013.01); *A61C 17/221* (2013.01); *B26B 19/042* (2013.01); *B26B 19/06* (2013.01); *B26B 19/20* (2013.01); *B26B 19/265* (2013.01); *B26B 19/38* (2013.01); *B26B 19/384* (2013.01); *B26B 19/386* (2013.01); *B26B 19/3806* (2013.01); *B26B 19/3813* (2013.01); *B26B 19/3873* (2013.01);
(Continued)

(58) Field of Classification Search
CPC ..... B26B 19/06; B26B 19/388; B26B 19/042; B26B 19/386; B26B 19/3886; B26B 19/48; B26B 19/3813; B26B 19/40; B26B 19/20; B26B 19/384; B26B 19/265; B26B 19/38; B26B 19/3806; B26B 19/3873; A61C 17/221

See application file for complete search history.

(56) References Cited

U.S. PATENT DOCUMENTS 6,233,535 B1    5/2001    Petretty
6,326,884 B1    12/2001    Wohlrabe
(Continued)

FOREIGN PATENT DOCUMENTS

EP    3 300 866 A1 *    4/2018
GB    1021836    3/1966
(Continued)

*Primary Examiner* — Hwei-Siu C Payer
(74) *Attorney, Agent, or Firm* — Ronald T. Sia; Kevin C. Johnson

(57) ABSTRACT

A personal care appliance comprises a head, a display device, and a drive unit including a motor for driving a removable tool element in the head via a drive transmitter. The head has at least one coupling element for coupling different types of tool elements with the drive transmitter. The tool elements comprises at least two of the following tool elements: a skincare unit, a long-hair cutting unit, a beard-trimming unit, a brush, and a short-hair cutting unit, wherein at least one mode button is provided for changing operating parameters of the motor and is configured to indicate upon activation at least one of the tool elements at the display device.

13 Claims, 6 Drawing Sheets

(51) Int. Cl.
- *B26B 19/04* (2006.01)
- *B26B 19/48* (2006.01)
- *B26B 19/40* (2006.01)
- *B26B 19/20* (2006.01)
- *A61C 17/22* (2006.01)
- *B26B 19/26* (2006.01)

(52) U.S. Cl.
CPC .......... *B26B 19/3886* (2013.01); *B26B 19/40* (2013.01); *B26B 19/48* (2013.01)

(56) References Cited

U.S. PATENT DOCUMENTS

| | | | |
|---|---|---|---|
| 8,141,253 B2* | 3/2012 | Royle | B26B 19/06 30/34.05 |
| 2005/0028371 A1 | 2/2005 | Kakimoto | |
| 2012/0192436 A1 | 8/2012 | Toy | |
| 2015/0246454 A1 | 9/2015 | Mintz et al. | |
| 2016/0307712 A1* | 10/2016 | Nishimura | G06F 3/023 |
| 2018/0085942 A1* | 3/2018 | Perez Lopez | B26B 19/042 |
| 2018/0085952 A1* | 3/2018 | Perez Lopez | B26B 19/042 |
| 2018/0085953 A1* | 3/2018 | Perez Lopez | B26B 19/042 |

FOREIGN PATENT DOCUMENTS

| | | |
|---|---|---|
| WO | WO 98/25736 | 6/1998 |
| WO | WO 2009/027928 | 3/2009 |
| WO | WO 2016/041929 | 3/2016 |
| WO | WO 2018/060846 A1 * | 4/2018 |

\* cited by examiner

ELECTRIC SHAVER

FIELD OF THE INVENTION

The present invention relates to a multipurpose personal care appliance to which different types of tooling elements such as a long-hair cutter, a short-hair cutter and a skincare unit can be attached.

BACKGROUND OF THE INVENTION

Electric shavers usually have one or more cutter elements driven by an electric drive unit in an oscillating manner where the cutter elements reciprocate under a shearfoil, wherein such cutter elements or undercutters may have an elongated shape and may reciprocate along their longitudinal axis. Other types of electric shavers use rotatory cutter elements which may be driven in an oscillating or a continuous manner. Said electric drive unit may include an electric motor or an electric-type linear motor, wherein the drive unit may include a drive train having elements such as an elongated drive transmitter for transmitting the driving motion of the motor to the cutter element, wherein the motor may be received within the handle portion of the shaver or in the alternative, in the shaver head thereof.

Such drive units are sometimes operable in different operation modes, wherein for example the cutter speed or oscillation frequency may be varied to increase shaving efficiency in a fast mode or highspeed mode, whereas power consumption may be reduced in a slow mode or low speed mode. Depending on the fittings of the shaver, other operation modes may be offered and may include a long-hair cutting mode in which the drive unit, in addition to or in the alternative to driving the at least one cutter unit, may drive a long hair cutter, or a fluid application mode in which a lubricating applicator such as a spray nozzle may be activated, or a ventilating mode in which a ventilator may be driven by the drive unit to generate airflow to achieve cooling or cleaning.

So as to give a user the option to choose between those different operation modes, the shaver may be provided with a mode input element such as a touch button, a toggle switch or a gesture sensor to allow the user to input a respective mode command switching the shaver's drive unit and/or a control unit into the desired operation mode. For example, document US 2015/0246454 A shows an electric shaver operable in more than one operating mode, wherein a mode input element is provided for switching the driving unit into different operation modes. Sometimes switching between different operation modes may be effected automatically, for example the aforementioned low speed mode may be chosen automatically when the battery charging level becomes low.

In order to give the user feedback which operation mode has been selected, such shavers may have a display device for displaying information about such operation mode. For example, the selected cutter speed may be indicated, or the activation of functional accessories such as the aforementioned fluid applicator or airflow generator may be displayed.

In addition or in the alternative to displaying such information on the operation mode, other information may be displayed by such display devices. For example, the charging status of a battery or accumulator of the shaver may be indicated, or the shaving time may be displayed, wherein such additional information also may be displayed when the shaver or the drive unit thereof is inactive. For example, it has been suggested to extend the activity of the display to a period of some seconds after switching off the shaver so that, for example, the battery charge level is indicated for some seconds after switching off the shaver and thereafter, fading out to the idle mode in which no information is displayed. Document WO 98/25736 A suggests to display certain shaver information on the shaver's charging/cleaning station which is provided with a display for displaying such data and communicates with the shaver for receiving user data from the shaver. It also has been suggested that the sleeping display can be waked up when the power button of the shaver is briefly touched.

Sometimes such shavers may be provided with additional personal care tools such as a skin treatment unit or a long-hair cutter unit or a beard trimmer. Such skin treatment units may comprise, for example, tooling elements such as a peeling tool, a massage brush or vibration elements for enhancing blood circulation. Such skincare tools can be fixedly or releasably attached to the head portion of the device. For example, document WO 2009/027928 A discloses a personal care appliance having a head provided with coupling means for coupling different types of tools with the drive transmitter, such tools including a vibrating safety razor, a hair trimming device and a comb attachment.

SUMMARY OF THE INVENTION

It is an objective underlying the present invention to provide for an improved electric personal care appliance avoiding at least one of the disadvantages of the prior art and/or further developing the existing solutions. A more particular objective underlying the invention is to provide for an improved displaying of information to the user.

A further objective underlying the invention is to provide for an improved control of information to be displayed to the user without sacrificing easy handling of the personal care appliance. More particularly, a self-explaining, intuitive handling and use of the information functions of the personal care appliance should be achieved.

A still further objective underlying the invention is to provide for an improved multipurpose personal care appliance offering improved operation of various tool elements such as a short-hair cutter, a long-hair cutter or a skin treatment unit.

To achieve at least one of the aforementioned objectives, the personal care appliance allows for changing the personal care tool attached to the head of the appliance. More particularly, the head of the personal care appliance may be provided with at least one coupling means allowing to couple different types of tool elements with the drive transmitter, wherein such exchangeable tool elements may include a skin care unit, a long hair cutting unit, a beard trimming unit, a brush and/or a short hair cutting unit. So as to adjust the driving parameters of the drive unit to the individual personal care tool that is used, the personal care appliance may include at least one mode button for changing at least one operating parameter of the motor. So as to present relevant information to a user and keep away irrelevant information, i.e. information relevant to a non-used, exchanged tool, from the user, said at least one mode button may be configured to indicated upon activation at least one of the aforementioned tool elements at the display device. The information displayed to a user may be tailored in response to the tool element attached to the appliance's head.

According to a further aspect, it is suggested to give the user the option to perceive different sets of information even when the personal care appliance is switched off and/or the personal care appliance's drive unit is inactive. More particularly, the electric personal care appliance is configured to allow the user to select a specific one of a plurality of different sets of information. According to a first aspect, different functions are assigned to the electric personal care appliance's mode input element in dependency of the electric personal care appliance being switched on or switched off. When the personal care appliance is switched on and/or the personal care appliance's drive unit is active, said mode input element is configured to switch the driving unit into different operation modes, whereas, when the personal care appliance is switched off and/or the personal care appliance's drive unit is inactive, said mode input element is configured to switch the display device into different display modes for displaying different sets of information. Such double function of the mode input element allows for a natural, intuitive handling of the personal care appliance as a user knowing the input element may be used to change the drive unit's operation modes when the personal care appliance is switched on, naturally will use such mode input element to change the display modes of the display device when the personal care appliance is inactive or switched off. In addition, due to such double function of the mode input element no additional button or key is necessary to switch the display modes and thus, space can be saved and an easy structure of the personal care appliance's input element can be maintained.

According to a further aspect, the personal care appliance's display device may be provided with an automatic switching mode in which different sets of information are displayed automatically one after the other under control of a timer. Such automatic switching mode keeps the user informed of any relevant information and, in addition, makes the user learn to know the personal care appliance's different information functions and different sets of information.

Such automatic switching mode of the display device may be activated in response to presence of a parameter indicative of the user being attentive and receptive and/or in response to a parameter indicative of a certain operational phase or status of the personal care appliance. In particular, said automatic switching mode may be activated when the personal care appliance is switched off and/or the drive unit becomes inactive. In the alternative or in addition, the automatic switching mode of the display device may be activated when the sleeping personal care appliance is touched or an object such as a finger or a hand is approaching the sleeping personal care appliance.

These and other advantages become more apparent from the following description giving reference to the drawings and possible examples.

DETAILED DESCRIPTION OF THE INVENTION

Figure 1:
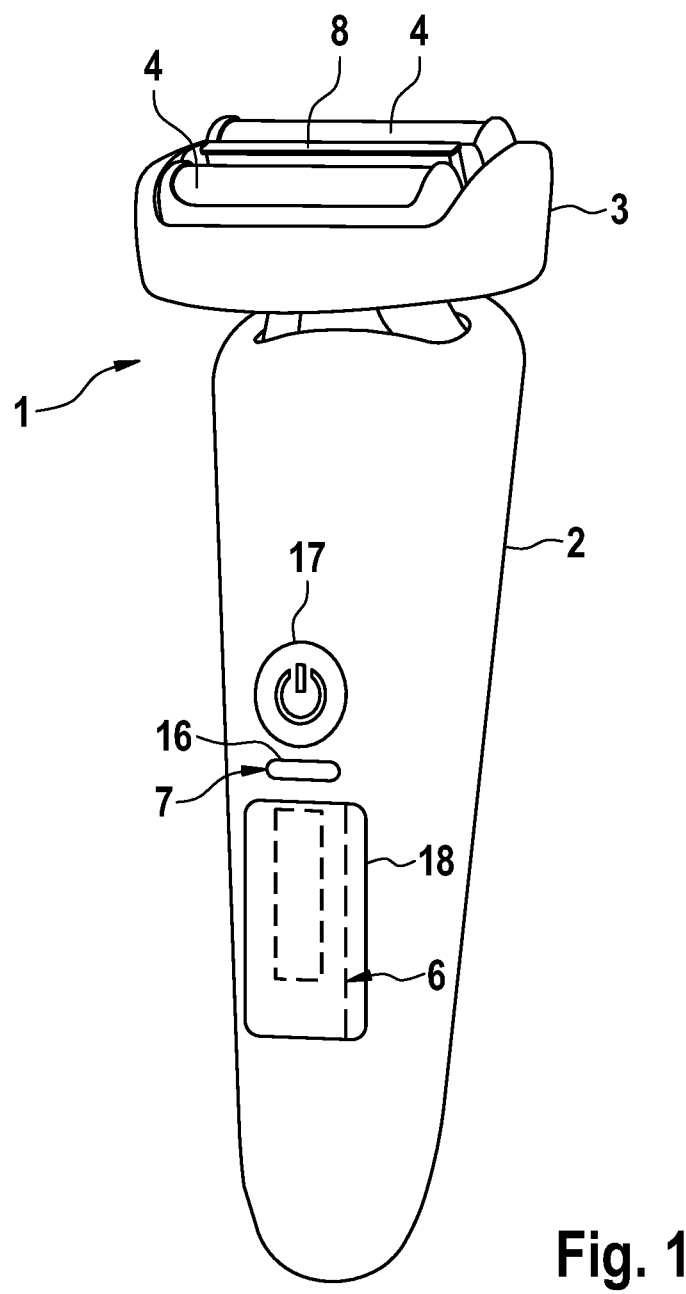
FIG. 1: a perspective view of an electric shaver comprising a handle and a shaver head connected thereto, wherein a display device of the shaver includes a display on the handle.

The electric shaver offers comfortable ways of communicating relevant information to the user, wherein according to one aspect the user actively may select the relevant information from a plurality of sets of information offered to be displayed. According to another aspect, the personal care appliance may automatically display different sets of information to the user at a convenient point of time once a user is attentive and ready to perceive such information.

More particularly, according to a first aspect, the mode input element which is configured to switch the active personal care appliance into different operation modes, is also configured to switch the display device into different display modes for displaying different sets of information when the drive unit is inactive and/or the shaver is sleeping. Thus, the mode input element is given a second function in addition to its genuine function of controlling the operation mode of the active personal care appliance.

When the personal care appliance is active and/or the drive unit is switched on, the mode input element may control the drive unit to operate either in a lower speed mode in which the tool is driven at a lower speed and/or at a lower oscillation frequency, or in a highspeed mode in which the tool is driven at a higher speed and/or at a higher oscillation frequency. Intermediate speed modes providing for tool speeds and/or tool oscillation frequencies between the aforementioned high speeds and low speeds also may be provided and switched on by the mode input element.

In addition to such speed control function, the input mode element also may be configured to control other grooming functions of the personal care appliance. For example, the mode input element may activate a long-hair cutter to be driven by the drive unit. In addition or in the alternative to such long-hair cutting mode, the mode input element also may switch the personal care appliance to operate in a short-hair shaving mode in which only the aforementioned at least one cutting unit is operated, wherein the long-hair cutter is switched into its inactive state. Other grooming functions such as applying lubricating and/or cooling fluid onto the skin, or blowing cooling/cleaning air onto the skin and/or onto the personal care appliance head may be available, wherein the mode input element may be configured to activate the applicator providing for such function such as a fluid applicator and/or an airflow generator.

In addition to such control of the operation modes, the mode input element may be configured to switch the display device of the personal care appliance into different display modes to display different sets of information. In particular, so as to be able to offer different sets of information, the personal care appliance may be provided with a plurality of detectors for detecting respective information and/or parameters indicative of such information. For example, the display device may be connected to a charging level detector for detecting the charging level of an accumulator or battery of the personal care appliance. A corresponding charge level signal provided by the charging level detector may be stored in a memory to which the display device has access and/or may be provided online to the display device. When the mode input element is used to switch to a charging level display mode, the mode input element may interact with the display device and/or a display controller thereof and/or said memory so as to make the display device to display the information on the charging level on the basis of the charging level signal of the detector.

In addition to or in the alternative, a personal care time and/or personal care run detector may be provided for detecting the personal care time and/or the number of personal care runs performed since a last cleaning run. The personal care time signal and/or personal care run signal provided by the detector may be stored in a memory to which the display device has access and/or may be provided directly to the display device, wherein the mode input element may be configured to switch the display device into a personal care time and/or personal care run display mode in which the display device and/or a display controller thereof effects displaying of a personal care time information and/or personal care run information on a display.

In addition or in the alternative, a cleaning status detector may detect the cleaning status of the personal care appliance, wherein such detector may detect, for example, the time expired since a last cleaning cycle and/or the amount of hair dust residing in the head and/or any other parameter indicative of the cleaning status. Again, such cleaning signal provided by the cleaning detector may be stored in a memory to which the display device has access and/or may be provided directly to the display device and/or a display controller thereof when the mode input element switches the display device into a cleaning status display mode so that the corresponding cleaning information is displayed.

In addition to or in the alternative, there may be also a wear detector for detecting wear and tear of the tool unit, wherein such wear detector may detect the number of personal care runs since the last replacement of the tool unit and/or the frictional resistance of the tool unit when oscillating, i.e. the oscillation resistance and/or driving power necessary to drive the tool unit, and/or any other parameter indicative of wear and tear of the tool unit. The wear signal of such wear detector may be stored in a memory and/or directly provided to the display device when the display device and/or a display controller thereof is caused by the input mode element to display a wear information on the basis of such wear signal.

Said mode input element may include a touch key or touch button which may be realized as a mechanical button or as a soft key in terms of, for example, a touch screen button so that the mode input element may be activated by pressing or touching the touch key. Such touch key or touch button may be configured to provide for a switch forward and switch backward function so that it is possible to switch from a first mode to a second mode and from a second mode to a first mode. For example, the touch key may be configured to differentiate between one click and two clicks as it is known from a computer mouse. Touching the key only once may, for example, provide for the aforementioned forward switching, whereas touching the key twice within a predetermined time may provide for the backward switching.

In addition or in the alternative to such touch key, the mode input element may include a gesture detector for detecting a finger gesture such as a finger wiping so as to allow for browsing through the various display modes by finger gestures. Such gesture detector also may be configured to provide for a forward switching and backward switching, wherein, for example, the direction of the finger wiping may be used to differentiate between backward and forward switching, wherein for example finger movements from left to right may be associated with forward switching whereas movements from the right to the left may provide for backward switching.

According to a further aspect, the mode input element may include a toggle switch button for toggling from one operation to another operation mode of the drive unit and toggling from one display mode to another display mode of the display device. If there are three or more operation modes or three or more display modes, toggling can be effected in a sort of circular fashion so that activating the toggle switch button a plurality of times effects switching from mode one to mode two to mode three to mode n and, when the last mode n is reached, further activation of the toggle switch button may cause switching from mode n to mode one again. In addition or in the alternative, such toggle switch button may be configured to provide for forward switching and backward switching as explained before.

According to a still further aspect, the mode input element may include a signal receiver and/or may be configured to be responsive to a received signal so as to switch the display modes and/or the motor operation modes and/or other functional operation modes in response to a received signal. Such mode switching signal may come from various electronic circuits and/or devices. In particular, the mode switch element may be responsive to a signal coming from an external device such as the charging and/or cleaning station or an electronic communication device such as a smartphone, a tablet or a laptop, thus allowing control of the display modes and/or motor operation modes and/or other functional operation modes by means of an external device.

The mode switch element also may receive a signal from a configuration detector detecting the configuration of the shaver and/or skincare device, wherein such configuration detector may detect, for example, the position and/or connection of a long-hair cutter, a beard trimmer and/or a skin treatment unit such as a brush or peeling device. If for example, a peeling device is attached to the personal care appliance head and/or moved into an active position, the mode switch element may switch the motor into a corresponding skin treatment mode to drive such skin treatment unit appropriately and/or may switch the display into a skin treatment display mode indicating relevant information about skin treatment.

The aforementioned mode input element may include a software module and/or a hardware module responsive to and/or processing such mode input signals and/or mode switching signals. More particularly, a micro controller may be provided for receiving the aforementioned signals and controlling the drive unit's motor and/or the display device in such different modes in response to the received signals, wherein such micro controller may include the aforementioned software and/or hardware elements.

The function associated with the mode input element may be determined in different ways or on the basis of different parameters. For example, the activation status of the drive unit, for example power consumption of the motor of the drive unit may be used as parameter on the basis of which the function of the mode input element may be determined.

For example, a detector may detect when the drive unit is active and working, wherein on the basis of a corresponding signal from such detector, the mode input element may be configured to switch the aforementioned operation modes of the personal care appliance. On the other hand, when the detector does not provide such signal or provides for an inactive signal indicating the drive unit is not working and/or the personal care appliance has been switched off, the mode button may be configured to switch the display modes. Thus, the mode input element may be responsive to a detector signal indicative of the personal care appliance being active or sleeping and/or indicative of the drive unit being switched on or switched off.

In addition to or in the alternative to the mode input element being responsive to the working/sleeping status of the drive unit or the personal care appliance, a shifting element can be provided for shifting the function of the mode input element from being configured to switch the operating modes to being configured to switch the displaying modes. Such shifting element gives the user the option to actively change the functions of the mode input element irrespective of the working/sleeping status of the personal care appliance and could include, for example, a touch key or touch button. It also would be possible that the shifting element and/or shifting function is integrated into the mode input element in terms of, for example, a detector for detecting activation time of the mode input element. For example, a brief, normal touching or clicking of the mode input element can be interpreted as a command for switching the operation mode or the display mode depending on the working/sleeping status of the personal care appliance, whereas on the other hand, a longer touching of the mode input element exceeding a predetermined period of time, for example three seconds, could be interpreted as a command for shifting the function of the mode input element. For example, when the personal care appliance is active and the drive unit works, pressing the mode input element for more than three seconds could be interpreted as a command for shifting into the display mode function allowing to shift the display modes of the display device.

According to a further aspect of the invention, the display device is configured to be operable in an automatic switching mode in which different sets of information are displayed one after the other under control of a timer so that each of the available sets of information or each of a predetermined subgroup of the available sets of information is displayed for a predetermined period of time one after the other on a display.

Such automatic switching mode of the display device can be activated in different ways and may form an aspect of a personal care appliance which does not have and does not need the aforementioned mode input element, but nevertheless may have such mode input element. According to a further aspect, activation is effected at a point of time where the user is attentive and, under normal circumstances, may perceive the automatically displayed information. For example, an activator may activate the automatic switching mode in response to a switching off signal indicating switching off the drive unit and/or indicating transition of the drive unit from being active to being inactive, and/or in response to a switch on signal indicating switching on the drive unit and/or indicating transition of the drive unit from being inactive to being active.

In the alternative or in addition, said automatic switching mode may be activated one an object such as a finger or a hand touches the sleeping personal care appliance and/or approaches the sleeping personal care appliance. To detect such approach, the personal care appliance, in particular the personal care appliance handle may be provided with a detector or sensor device capable of detecting an object such as a finger or a hand approaching the personal care appliance. Such detector may include a touch sensor and/or an opticle sensor or any other sensor capable of detecting a finger in its neighborhood.

The display device may include a display on the handle, wherein such display may include, for example, an LED display device or other suitable display types.

In order to achieve a space-saving display arrangement, the display device may include at least one display field which is used for displaying information relative to the operation modes as well as information relative to other aspects of the shaver such as the aforementioned charging level, shaving time, cleaning status or wear and tear status. For example, such display field may be configured to display pictograms such as a cascade or row of display points or LEDs.

In addition or in the alternative to a display provided on the personal care appliance itself, a display may be provided on a cleaning and/or loading station configured to receive and/or be connected to the personal care appliance so as to charge the personal care appliance's battery and/or clean the personal care appliance, wherein a fluid may be applied to the head to clean the personal care appliance. Such cleaning and/or charging station may include a display device configured to communicate with the personal care appliance at least when the personal care appliance is docked into the station so as to display the aforementioned information. The display at the cleaning and/or charging station may be controlled by means of the personal care appliance's mode input element and/or in the aforementioned automatic switching mode automatically switching from one display mode to another display mode.

The display device of the cleaning and/or charging station may be controlled from the personal care appliance and/or by means of input elements at the station itself. To allow for control of the station's display from the personal care appliance, the personal care appliance and the station may be provided with data communication interfaces which may include physical connection elements that can be brought into contact with each other when the personal care appliance is docked into the station, and/or wireless communication elements such as bluetooth or other nearfield communication interfaces.

According to a further aspect, the electric personal care appliance may provide for automatic indication of the personal care appliance head's dirt status. Cut hair or other debris such as dust or dirt is usually accumulated within the interior space of the personal care appliance head below the personal care appliance head's cutter unit. From time to time, such interior space of the personal care appliance head needs to be cleaned. To remind the user of cleaning when it is necessary or to automatically control and/or initiate such cleaning, the personal care appliance may be provided with a dirt measurement unit measuring at least one parameter that is related to the dirt status and/or the amount of dirt accumulated in the personal care appliance head.

For example, said measurement unit may measure relevant parameters such as shaving time and/or shaving resistance and/or frictional resistance of a cutter element and/or power consumption of the drive unit during shaving and/or contact pressure (as users tend to increase contact pressure when shaving performance decreases) and/or electrical signals of sensor elements such as electric resistance sensors responsive to hair/dust coating or optical sensors, or other parameters indicative of debris in the personal care appliance head.

A micro controller may analyze such measured parameters to determine the dirt status of the personal care appliance head and may cause an indicating means to give a user an indication signal or information about the dirt status which may be, for example, displayed on the aforementioned display device. In addition or in the alternative, the micro controller may provide a signal to the cleaning station to automatically initiate a cleaning cycle in response to the determined dirt status and/or a signal to a smart phone to display the dirt status there.

These and other features become more apparent from the example showing in the drawings. As can be seen from FIG. 1, the shaver 1 may have a shaver housing forming a handle 2 for holding the shaver, which handle may have different shapes such as—roughly speaking—a substantially cylindrical shape or box shape or bone shape allowing for economically grabbing the shaver.

On one end of the shaver 2, a shaver head 3 is attached to the handle, wherein the shaver head 3 may be slewably supported about one or more slewing axes.

The shaver head 3 includes at least one cutter unit 4 which may include a cutter element or undercutter reciprocating under a shearfoil. The shaver head 3 may also include a long hair cutter 8 as it is shown by FIG. 1.

So as to drive such cutter unit 4 and the long hair cutter 8, a drive unit may include a motor that can be received within the handle 2 and can be connected to the cutter unit 4 and the long hair cutter 8 by means of a transmitter or drive train extending from the motor to the cutter unit.

As can be seen from FIG. 1, an ON-OFF switch or power switch 17 may be arranged at the handle 2, for example on a front side of said handle 2. By means of such power switch 17, the drive unit may be started and switched off again.

As can be seen from FIGS. 2 to 6, the shaver 1 further includes a display 18 which may be provided on the handle 2, for example on a front side thereof. Such display 18 may be part of a display device 6 further including additional electronic components or other elements such as a display controller 11, a memory, power supply components etcetera.

Figure 3:
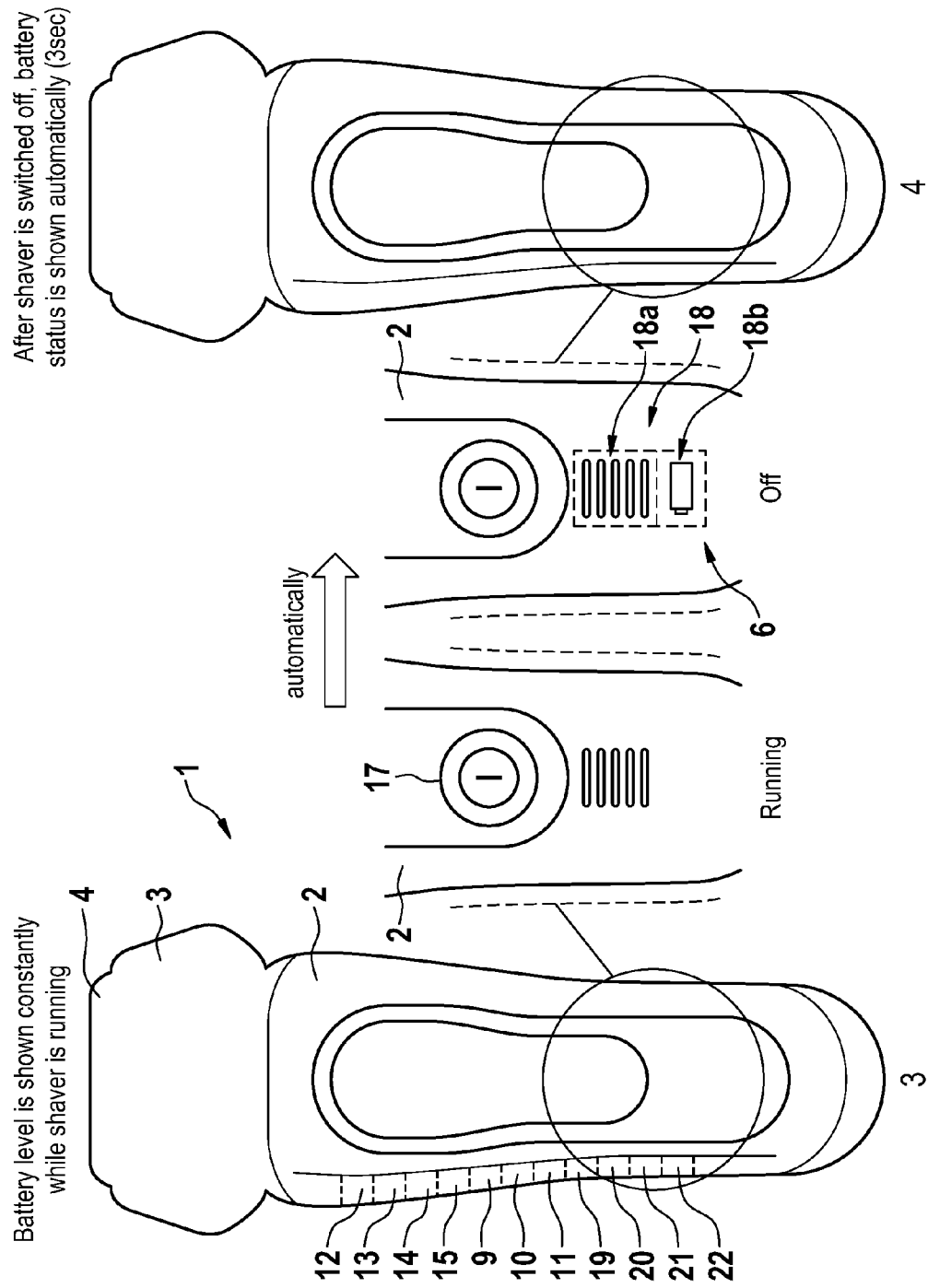
Figure 4:
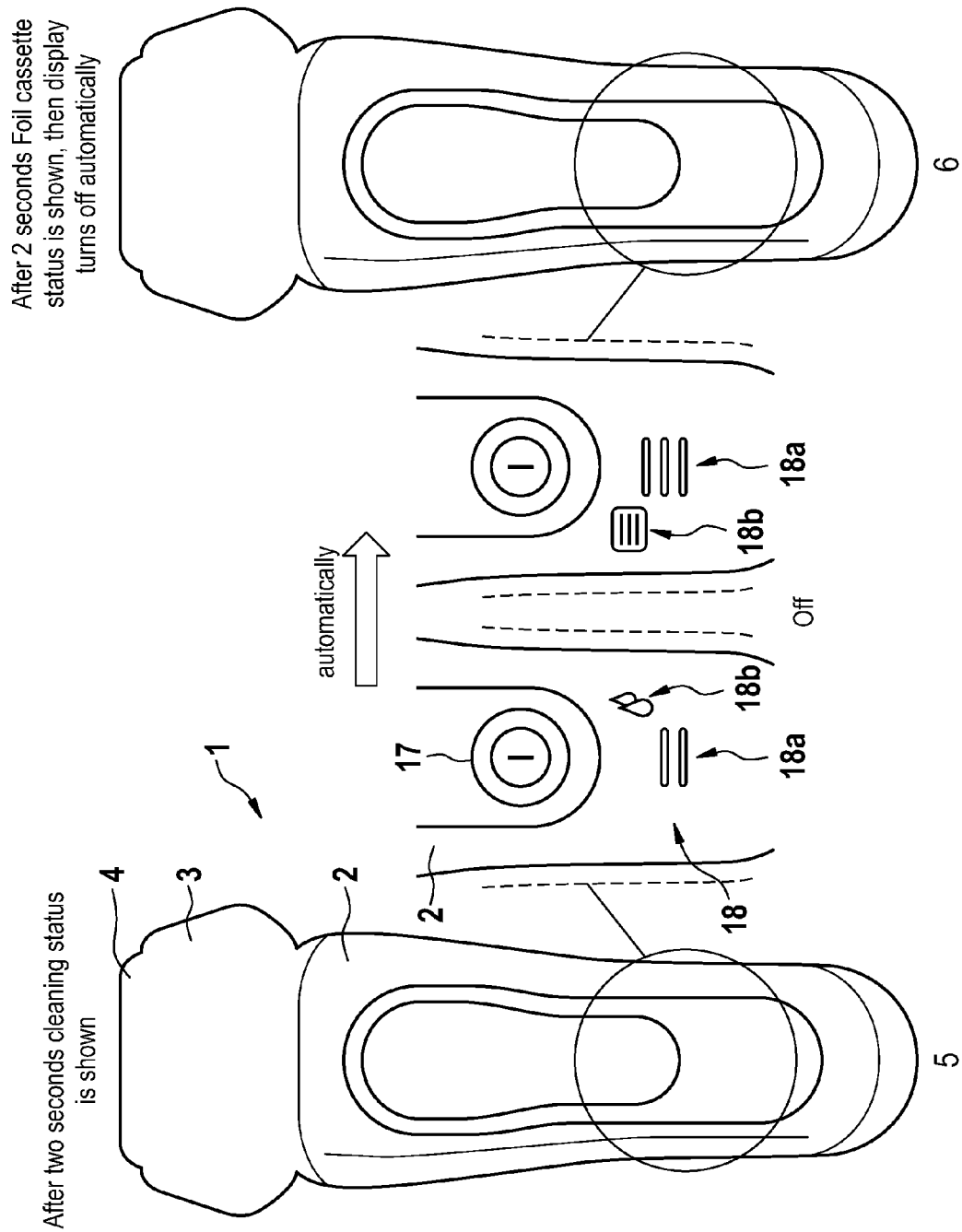
FIG. 4: a schematic view of the shaver's display in still further display modes to further illustrate the automatic switching mode of the display device, wherein a transition between two further display modes is shown after having switched off the shaver's drive unit.

The display 18 may include a first display field 18a comprising an LED cascade and a second or further display field 18b where symbols and/or pictograms indicative of the type of information to be displayed can be shown and displayed, cf. FIGS. 3 and 4.

Figure 5:
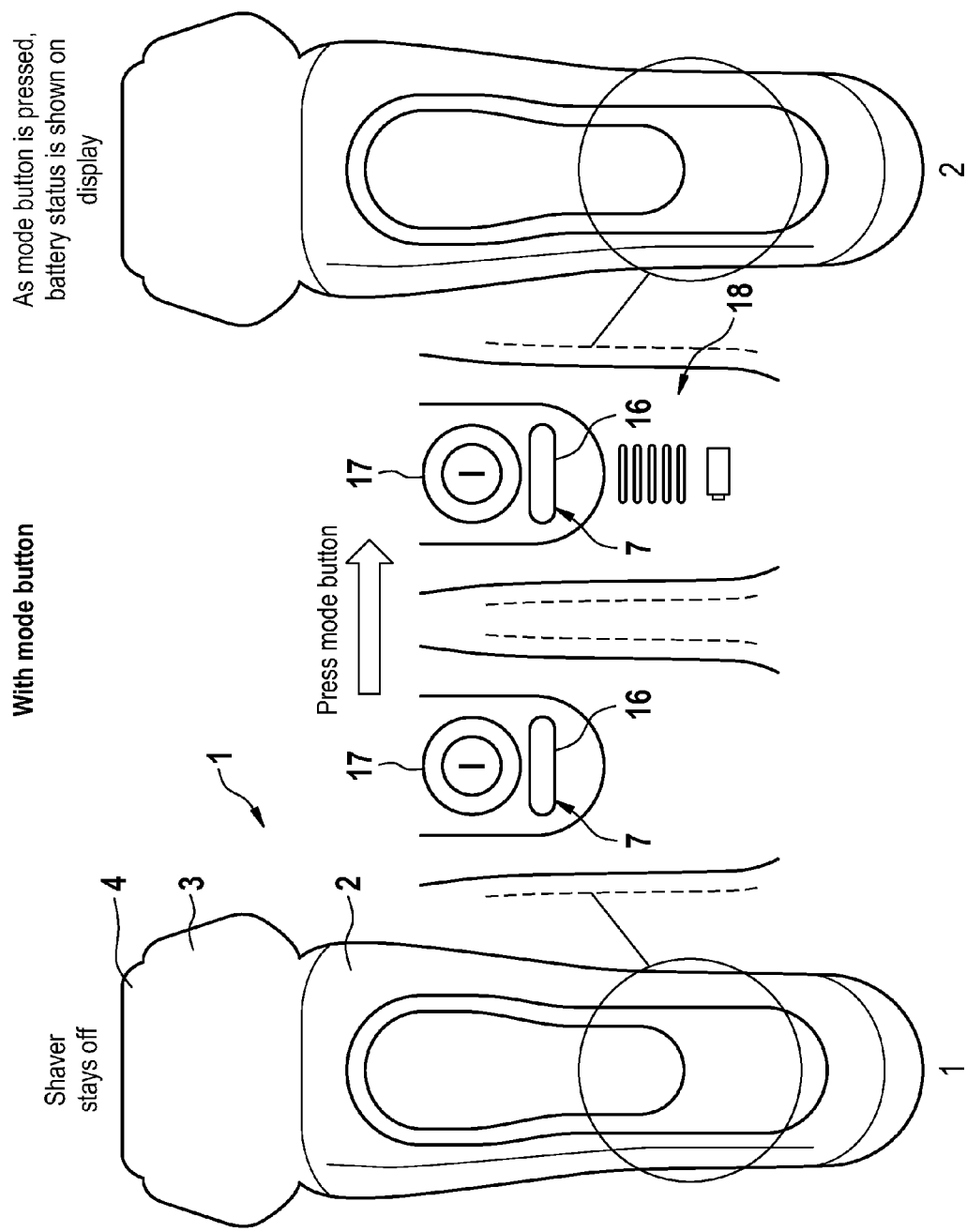
FIG. 5: a schematic view of the shaver's display and the shaver's mode input element, wherein use of such mode input element is illustrated when the shaver is switched off, wherein different display modes of the display as selected by the mode input element are illustrated.

As can be seen from FIG. 5, the shaver 1 may further include a mode input element 7 in terms of, for example, a touch button 16 which may be positioned in the neighborhood of the power switch 17.

As illustrated by the figures, the display device 6 may work in an automatic mode and in addition, in a manually controlled mode. For example, when starting the shaver 1 by touching the power switch 17, the display 18 may show a cascade of light signals so as to indicate that the shaver is wakening up. For example, after starting with only one light blinking or lighting, the number of the lighting LEDs may be increased one by one until all LED of the cascade are lightening.

Figure 2:
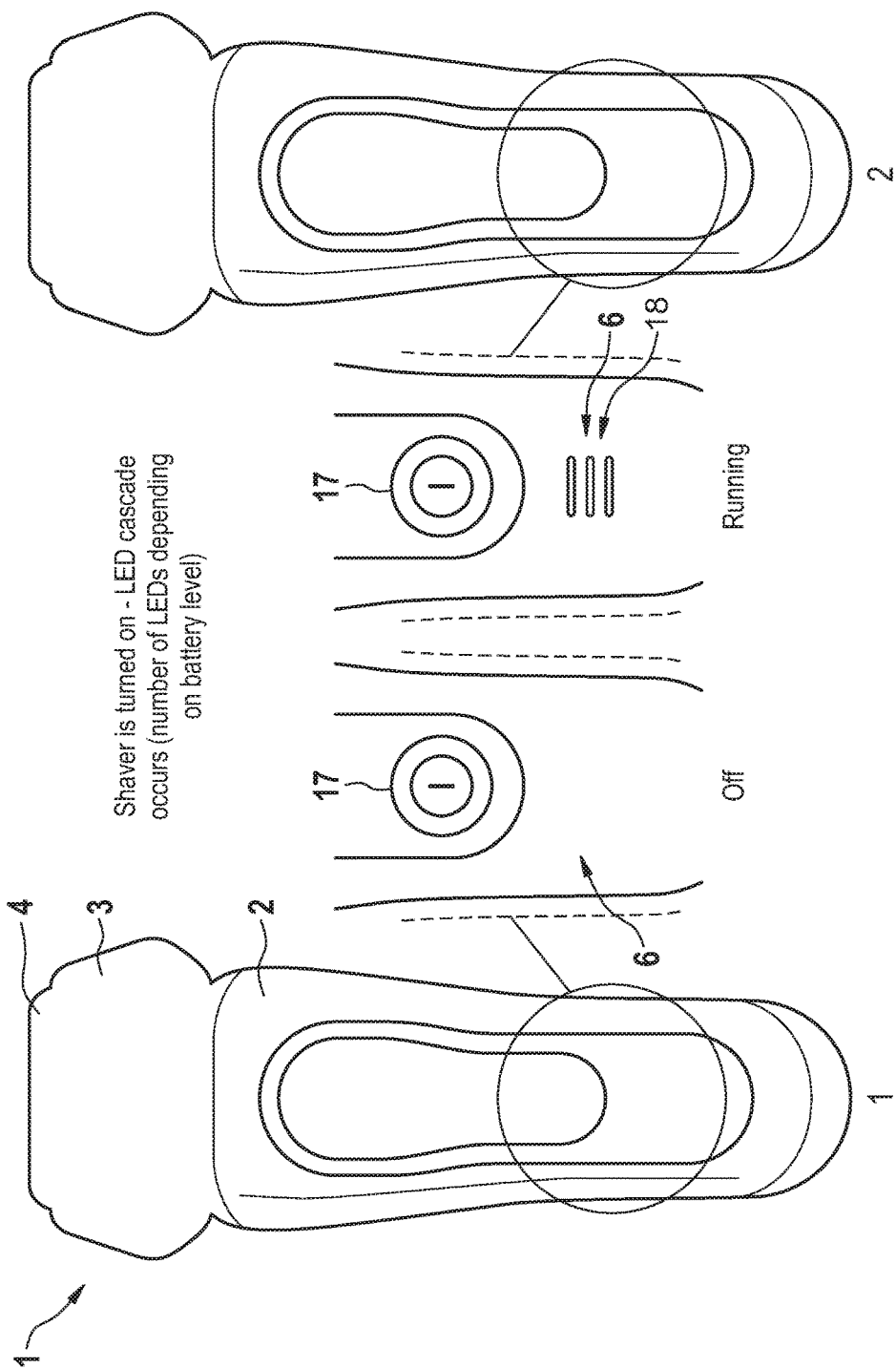
FIG. 2: a schematic view of the shaver's display in different display modes, illustrating the display's transition when the shaver is turned on, FIG. 3: a schematic view of the shavers' display in further different display modes to further illustrate the display devices automatic switching mode, wherein a transition of the display is shown when the shaver's drive unit is switched off.

After such initialization procedure or in the alternative thereto, the display 18 may display the battery level, wherein the number of the cascade bars lightening may correspond to the battery level, cf. FIG. 2.

As can be seen from FIG. 3, the display 18 may continue to display the battery level for a predetermined period of time after the shaver has been switched off. For example, the battery status may be shown automatically for three seconds, cf. FIG. 3 right side.

According to an aspect, the display 18, after switching off the shaver, does not only show the charging level, but automatically switches into other display modes to display other sets of information. Such automatic switching mode of the display device 6 may have been activated by an activator 10 in response to a parameter indicating switching off the shaver. Such activator may be responsive to a detector signal or a parameter indicative of switching off the shaver.

In addition or in the alternative, the automatic switching mode of the display device 6 also may be activated by said activator 10 in response to a parameter indicating approximation of an object or subject to the shaver 1, in particular a finger or a hand portion approaching or touching the shaver 1.

Thus, the activator 10 may be configured to responsive, when the shaver is sleeping, to a detector signal of an approximation detector or contact sensor 19.

As can be seen from FIG. 4, due to such automatic switching mode, the display 18 may display, after having displayed the charging level, the cleaning status, cf. FIG. 4 left side and thereafter, the cutter unit's status, cf. FIG. 4 right side. Such automatic switching of the display modes may be effected under time control of a timer 9.

As can be seen from FIGS. 3 to 4, the display 18 may indicate in its second display field 18b the type of information displayed, wherein a respective information type symbol such as a battery, cleaning fluid drops or a foil cassette symbol or other pictograms may be shown.

Figure 6:
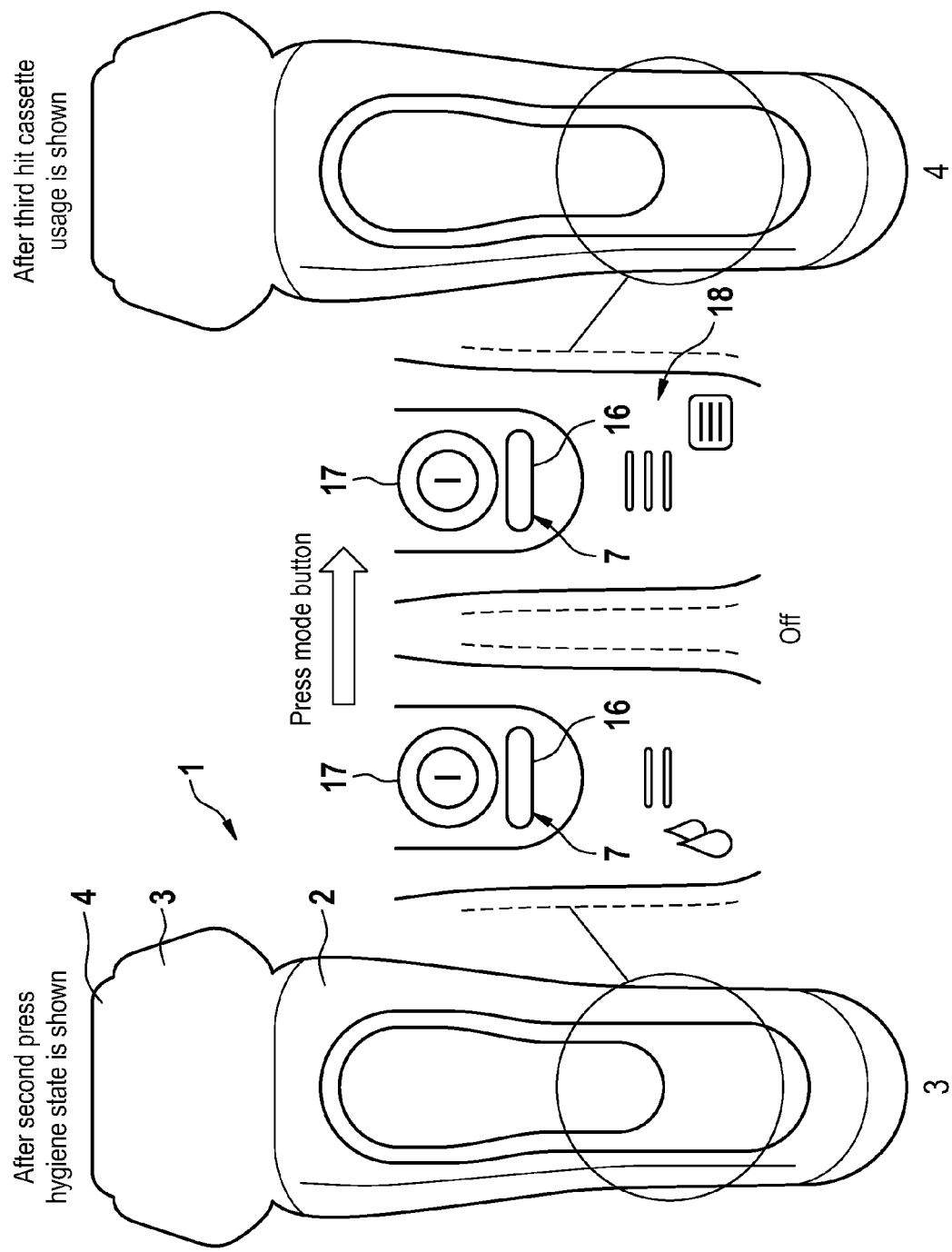
FIG. 6: a schematic view of the shaver's display in further different display modes as selected by the mode input element when the shaver's drive unit is inactive.

As can be seen from FIGS. 5 and 6, the display modes of display device 6 also can be switched manually by means of using the aforementioned mode input element 7 which, in its genuine function may be used to switch the operation modes of the active shaver such as cutting speed, oscillation frequency etcetera. When the shaver is sleeping and/or has been switched off, the display also may go into a sleeping mode, cf. FIG. 5 left side. When activating or touching the mode input element 7, the display is wakening up and first may show the battery charging level, cf. FIG. 5 right side.

By means of touching or activating the mode input element 7 once again or further times, the display device 6 is caused to switch into other display modes to display other sets of information such as the cleaning status, cf. FIG. 6 left side and the cutter unit status, cf. FIG. 6 right side.

As can be seen from FIG. 3, the shaver 1 further may be provided with a dirt measurement unit 20 for measuring parameters relevant to the dirt status, wherein such measurement unit 20 may include a voltage and/or current detector for detecting power consumption of the drive unit during shaving and/or a time measurement means for measuring shaving time, for example.

A micro controller 21 may receive signals indicative of such parameters and may analyze such signals to determine the dirt status, wherein indicating means 22 such as the described display device 6 may be controlled by the micro controller 21 to indicate to a user the dirt status. In addition or in the alternative, such dirt status information may be communicated to a charging and/or cleaning station to automatically initiate a cleaning cycle in response to the dirt status.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal care appliance, comprising a handle and a head, wherein said handle is provided with an ON/OFF power button, a display device, a drive unit including a motor for driving a moveable tool element in the head via a drive transmitter, wherein said head comprises a coupling member for receiving and engaging different types of tool elements with the drive transmitter, said tool elements comprising at least two of the following tool elements: a skincare unit, a long-hair cutting unit, a beard-trimming unit, a brush, and a short hair cutting unit, wherein at least one mode button is provided for changing operating parameters of said motor, wherein said at least one mode button is configured to indicate upon activation at least one of the aforementioned tool elements at the display device.

2. The personal care appliance according to claim 1, wherein said drive unit, when being active, is operable in more than one operation mode, wherein a mode input element is provided for switching the drive unit into different operation modes, wherein said mode input element is configured to switch the display device into different display modes for displaying a first set of information when said drive unit is active and a second set of information when said drive unit is inactive.

3. The personal care appliance according to claim 2, wherein said mode input element is configured to be responsive to a signal received from at least one of the following: an external control device, a smartphone, a charging and/or cleaning station, a mode input button, the power ON/OFF button, a skincare configuration detection unit for detecting the type of attachment attached to the handle, a wake up sensing unit for detecting a waking up situation, and a timer.

4. The personal care appliance according to claim 2, wherein said mode input element includes at least one push button configured to change its functionality depending from an ON/OFF status of the drive unit.

5. The personal care appliance according to claim 2, wherein said operation modes of the drive unit includes at least one of the following
a lower speed mode in which at least one of said tool elements is driven at a lower speed,
a higher speed mode in which at least one of said tool elements is driven at a higher speed,
said long-hair cutting unit mode in which a long-hair cutter is driven by said drive unit, and
a short-hair shaving mode in which said short hair cutting unit is driven by said drive unit,
a brush attachment mode in which said skincare unit is driven by said drive unit, and
said beard-trimming attachment mode in which a beard trimmer unit is driven by said drive unit.

6. The personal care appliance according to claim 2, wherein said different display modes include at least one of the following:
a charge information mode in which the charging status of an accumulator is displayed,
a treatment time and treatment runs information mode in which the treatment time and the number of treatment runs performed since a last cleaning run is displayed,
a cleaning information mode in which a cleaning status of the personal care appliance
is displayed, and
a wear information mode.

7. The personal care appliance according to claim 2, wherein said display device is under control of an electronic controller which is connected to at least one detector for providing at least one detector signal indicative of an information to be displayed, wherein said controller is responsive to a signal from said mode input element to display said information on the basis of the received detector signal indicative of said information when said mode input element has been activated to request displaying of said information.

8. The personal care appliance according to claim 2, wherein said mode input element includes
a toggle switch button for toggling from one operation mode to another operation mode of the drive unit and toggling from one displaying mode to another displaying mode of said display device,
a touch screen input element, and
a gesture detector for detecting a finger gesture.

9. The personal care appliance according to claim 1, wherein said display device is configured to be operable in an automatic switching mode in which different sets of information are displayed one after the other under control of a timer.

10. The personal care appliance according to claim 9, wherein an activator is provided for activating said automatic switching mode, wherein said activator is responsive to a switching off-signal indicating switching off the drive unit and indicating transition of the drive unit from being active to being inactive, and responsive to a switching on-signal indicating switching on the drive unit and indicating transition of the drive unit from being inactive to being active.

11. The personal care appliance according to claim 9, wherein a detector is provided for detecting objects or subjects touching and approximating the personal care appliance, wherein an activator is provided for activating said automatic switching mode, wherein said activator is configured to be responsive, when said personal care appliance is sleeping, to a touching/approximation signal of said detector to activate the automatic switching mode when an object or subject is touching and approximating the personal care appliance.

12. The personal care appliance according to claim 1, wherein said display device includes a first display field indicative of a value and an amount of an information, and a second display field indicative of the type of information, wherein said display device is configured to activate and operate said first display field in combination with different types of information displayed by said second display field.

13. The personal care appliance according to claim 1, wherein said display device includes a display arranged at the handle of the personal care appliance and/or is configured to control and communicate with an external display separate from said handle.

* * * * *